US012569835B2

(12) United States Patent
Kang et al.

(10) Patent No.: US 12,569,835 B2
(45) Date of Patent: Mar. 10, 2026

(54) AMMOXIDATION CATALYST FOR PROPYLENE, MANUFACTURING METHOD OF THE SAME CATALYST, AMMOXIDATION METHOD USING THE SAME CATALYST

(71) Applicant: LG CHEM, LTD., Seoul (KR)

(72) Inventors: Kyungyeon Kang, Daejeon (KR); Ji Yeon Kim, Daejeon (KR); Jun Seon Choi, Daejeon (KR)

(73) Assignee: LG CHEM, LTD., Seoul (KR)

( * ) Notice: Subject to any disclaimer, the term of this patent is extended or adjusted under 35 U.S.C. 154(b) by 965 days.

(21) Appl. No.: 17/778,744

(22) PCT Filed: Jul. 13, 2021

(86) PCT No.: PCT/KR2021/008936
§ 371 (c)(1),
(2) Date: May 20, 2022

(87) PCT Pub. No.: WO2022/015003
PCT Pub. Date: Jan. 20, 2022

(65) Prior Publication Data
US 2023/0057640 A1 Feb. 23, 2023

(30) Foreign Application Priority Data
Jul. 14, 2020 (KR) ........................ 10-2020-0087104

(51) Int. Cl.
| | |
|---|---|
| *B01J 23/887* | (2006.01) |
| *B01J 21/08* | (2006.01) |
| *B01J 35/31* | (2024.01) |
| *B01J 35/38* | (2024.01) |
| *B01J 35/40* | (2024.01) |
| *B01J 35/64* | (2024.01) |
| *B01J 37/02* | (2006.01) |
| *B01J 37/04* | (2006.01) |
| *B01J 37/08* | (2006.01) |
| *C07C 253/26* | (2006.01) |
| *B01J 35/30* | (2024.01) |
| *B01J 35/50* | (2024.01) |

(52) U.S. Cl.
CPC ........... *B01J 23/8876* (2013.01); *B01J 21/08* (2013.01); *B01J 35/38* (2024.01); *B01J 35/40* (2024.01); *B01J 35/647* (2024.01); *B01J 37/0221* (2013.01); *B01J 37/0236* (2013.01); *B01J 37/04* (2013.01); *B01J 37/088* (2013.01); *C07C 253/26* (2013.01); *B01J 35/31* (2024.01); *B01J 35/397* (2024.01); *B01J 35/50* (2024.01); *B01J 2235/00* (2024.01)

(58) Field of Classification Search
CPC .................................................... C07C 253/26
See application file for complete search history.

(56) References Cited

U.S. PATENT DOCUMENTS

| | | | |
|---|---|---|---|
| 4,264,476 A | 4/1981 | Umemura et al. | |
| 4,388,223 A | 6/1983 | Ferlazzo et al. | |
| 6,143,690 A | 11/2000 | Komada et al. | |
| 6,245,931 B1 | 6/2001 | Aoki et al. | |
| 7,473,666 B2 | 1/2009 | Yanagi et al. | |
| 10,137,437 B2 * | 11/2018 | Sokolovskii | B01J 23/8872 |
| 2005/0209491 A1 | 9/2005 | Ryu | |
| 2006/0155139 A1 | 7/2006 | Yanagi et al. | |
| 2006/0199730 A1 | 9/2006 | Seely et al. | |
| 2008/0015364 A1 | 1/2008 | Estenfelder et al. | |
| 2008/0286186 A1 | 11/2008 | Teshigahara et al. | |
| 2009/0118531 A1 | 5/2009 | Hibst et al. | |
| 2014/0194642 A1 | 7/2014 | Endo et al. | |
| 2015/0065744 A1 | 3/2015 | Watanabe et al. | |
| 2015/0151292 A1 | 6/2015 | Suh et al. | |
| 2015/0238939 A1 | 8/2015 | Yoshida et al. | |
| 2016/0051967 A1 | 2/2016 | Sokolovskii et al. | |
| 2018/0222850 A1 | 8/2018 | Li et al. | |
| 2018/0222851 A1 | 8/2018 | Lugmair et al. | |
| 2021/0070693 A1 | 3/2021 | Morii et al. | |

FOREIGN PATENT DOCUMENTS

| | | |
|---|---|---|
| CN | 1585673 A | 2/2005 |
| CN | 1744949 A | 3/2006 |
| CN | 102371156 A | 3/2012 |
| CN | 110214054 A | 9/2019 |
| CN | 110813284 A | 2/2020 |
| JP | S55-056839 A | 4/1980 |
| JP | S57-171437 A | 10/1982 |
| JP | H05-214024 A | 8/1993 |
| JP | 2006061888 A | 3/2006 |

(Continued)

OTHER PUBLICATIONS

Thanh-Binh et al. "Ammoxidation of Acrolein to Acrylonitrile Over Bismuth Molybdate Catalysts", Applied Catalysis a General, vol. 520 (2016), pp. 7-12.

*Primary Examiner* — Sikarl A Witherspoon

(74) *Attorney, Agent, or Firm* — BRYAN CAVE LEIGHTON PAISNER LLP

(57) ABSTRACT

The present disclosure relates to an ammoxidation catalyst for propylene, a manufacturing method of the same, and an ammoxidation method of propylene using the same. Specifically, in one embodiment of the present disclosure, there is provided a catalyst having a structure in which a metal oxide is supported on a silica support having a narrow particle size distribution, and excellent wear resistance.

18 Claims, 1 Drawing Sheet

(56)             References Cited

FOREIGN PATENT DOCUMENTS

| | | | |
|---|---|---|---|
| JP | 4095353 | B2 | 6/2008 |
| JP | 2012-510355 | A | 5/2012 |
| JP | 2016-520418 | A | 7/2016 |
| JP | 2017-132737 | A | 8/2017 |
| JP | 2017-171659 | A | 9/2017 |
| JP | 2020-506047 | A | 2/2020 |
| KR | 1020050098270 | A | 10/2005 |
| KR | 10-2006-0132811 | A | 12/2006 |
| KR | 10-0687671 | B1 | 3/2007 |
| KR | 10-0939143 | B1 | 1/2010 |
| KR | 10-2016-0002892 | A | 1/2016 |
| KR | 10-2016-0066922 | A | 6/2016 |
| KR | 10-2016-0083698 | A | 7/2016 |
| WO | 2010-060648 | A1 | 6/2010 |
| WO | 2012-144369 | A1 | 10/2012 |
| WO | 2019-187786 | A1 | 10/2019 |

* cited by examiner

【FIG. 1】
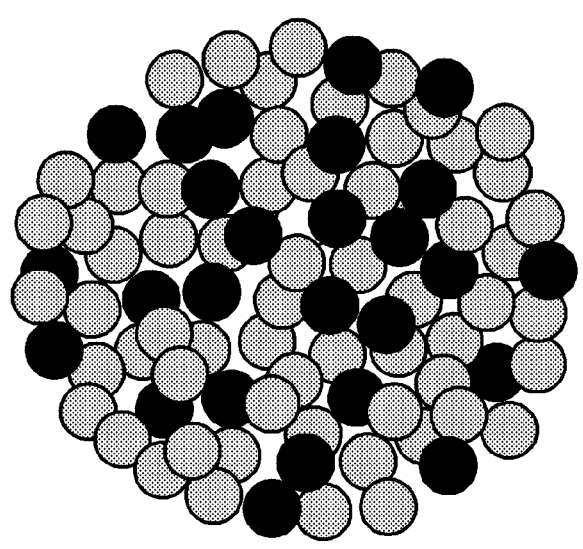
【FIG. 2】
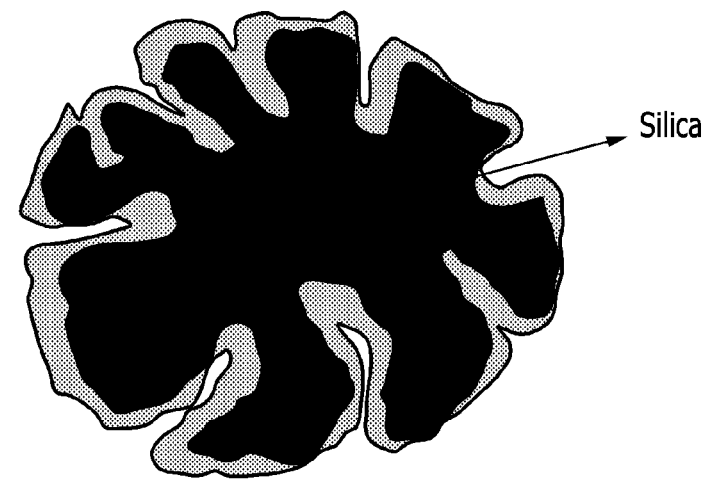
Silica

AMMOXIDATION CATALYST FOR PROPYLENE, MANUFACTURING METHOD OF THE SAME CATALYST, AMMOXIDATION METHOD USING THE SAME CATALYST

The present application is a National Phase entry pursuant to 35 U.S.C. § 371 of International Application No. PCT/KR2021/008936 filed on Jul. 13, 2021 and claims priority to and the benefit of Korean Patent Application No. 10-2020-0087104 filed on Jul. 14, 2020 with the Korean Intellectual Property Office, the disclosures of which are incorporated herein by reference in their entirety.

FIELD

The present disclosure relates to an ammoxidation catalyst for propylene, a manufacturing method of the same, and an ammoxidation method of propylene using the same.

BACKGROUND

Acrylonitrile may be prepared through an ammoxidation reaction of propylene.

Specifically, the ammoxidation reaction of propylene includes a reduction reaction of ammonia and propylene and a reoxidation reaction by oxygen, and a fluidized bed reactor is generally used to control heat generated during these reactions.

Since a molybdenum (Mo)-bismuth (Bi) oxide catalyst was proposed as a catalyst for ammoxidation of propylene, catalysts to which metals having various oxidation states are added have been proposed. However, despite the diversification of the catalyst composition, research on the structure and physical properties thereof is insufficient, and thus there is a limit to increasing the yield of acrylonitrile.

Specifically, a sol-gel method is widely known as a method for preparing an ammoxidation catalyst for propylene, which corresponds to a method in which a metal precursor solution and silica sol are co-precipitated and the co-precipitation product is spray-dried, followed by calcination.

According to the sol-gel method, a catalyst having a secondary particle structure in which metal oxide particles and silica particles are aggregated is prepared. Due to the weak binding force of the particles constituting the secondary particles, the particles are worn out in a flow reactor or split into primary particles such that they easily lose their catalytic activity. Accordingly, when using the catalyst prepared by the sol-gel method, it is necessary to continuously replenish the catalyst during the ammoxidation reaction of propylene, and even if the catalyst is replenished, there is a limit to increasing the yield of acrylonitrile.

Moreover, the catalyst prepared by the sol-gel method may already contain a large amount of fine powder before being introduced into the flow reactor. In the process of spray-drying the co-precipitation product of the metal precursor solution and the silica sol, the product may not be aggregated to an appropriate size and thus fine powder may be generated. Accordingly, the catalyst prepared by the sol-gel method has a problem in that productivity per se is low and manufacturing cost is high.

SUMMARY

There is provided an ammoxidation catalyst for propylene having a low content of fine powder and excellent durability, and it is possible to prepare acrylonitrile at a higher yield by using the catalyst.

Specifically, in one embodiment of the present disclosure, there is provided a catalyst having a structure in which a metal oxide with a specific composition is supported on a silica support in which a pore diameter and an apparent density are each controlled to a specific range.

According to one aspect, there is provided n ammoxidation catalyst for propylene comprising: a silica support containing a pore having a diameter of 2 to 15 nm and an apparent density of 0.25 to 1.0 g/cc; and a metal oxide supported on the silica support and comprising molybdenum (Mo), bismuth (Bi) and a dissimilar metal.

According to a further aspect, there is provided a manufacturing method of an ammoxidation catalyst for propylene comprising the steps of: preparing a first precursor aqueous solution containing a Mo precursor; preparing a second precursor aqueous solution containing a Bi precursor and a dissimilar metal precursor; supporting a mixture of the first and second precursor aqueous solutions on a silica support containing a pore having a diameter of 2 to 15 nm and an apparent density of 0.25 to 1.0 g/cc; drying the silica support on which the mixture of the first and second precursor aqueous solutions is supported; and calcining the dried material.

The catalyst of one embodiment may be prepared by an impregnation method, and may have a lower content of fine powder and excellent durability compared to a catalyst prepared by a sol-gel method.

In addition, the catalyst may exhibit improved durability while having a more uniform particle size distribution depending on the composition of the metal oxide, and the pore diameter and apparent density of the silica support.

Thus, when using the catalyst of one embodiment, acrylonitrile can be mass-produced at a high yield without additional supply of the catalyst during the ammoxidation process of propylene in a fluidized bed reactor.

BRIEF DESCRIPTION OF THE DRAWINGS

FIG. 1 schematically shows a catalyst having a secondary particle structure prepared by using a co-precipitation method.

FIG. 2 schematically shows the catalyst according to one embodiment.

DETAILED DESCRIPTION

As the present invention can be variously modified and have various embodiments, specific embodiments thereof are shown by way of examples and will be described in detail. However, it is not intended to limit the present invention to the particular form disclosed and it should be understood that the present invention includes all modifications, equivalents, and replacements within the idea and technical scope of the present invention. In describing the present invention, if it is determined that a detailed description of the related art may obscure the gist of the present invention, the detailed description thereof will be omitted.

In addition, the terms including ordinal numbers such as first, second, etc. to be used below may be used to describe various elements, but the elements are not limited by the terms. The above terms are used only for the purpose of distinguishing one component from another. For example, without departing from the scope of the present invention, a first component may be referred to as a second component, and similarly, a second component may also be referred to as a first component.

The singular forms are intended to include the plural forms as well, unless the context clearly indicates otherwise. It will be further understood that the terms "include", "comprise", or "have" when used in this specification, specify the presence of stated features, numbers, steps, operations, components, parts, or combinations thereof, but do not preclude the presence or addition of one or more other features, numbers, steps, operations, components, parts or combinations thereof.

Hereinafter, "particle diameter Dv" means a particle diameter at the v % point of the cumulative volume distribution according to particle diameters. In other words, D50 is a particle diameter at the 50% point of the cumulative volume distribution according to particle diameters, D90 is a particle diameter at the 90% point of the cumulative volume distribution according to particle diameters, and D10 is a particle diameter at the 10% point of the cumulative volume distribution according to particle diameters.

Hereinafter, the ammoxidation catalyst for propylene of one embodiment will be described in detail with reference to the drawings.

Ammoxidation Catalyst for Propylene

In one embodiment of the present disclosure, there is provided an ammoxidation catalyst for propylene including: a silica support containing a pore having a diameter of 2 to 15 nm and an apparent density of 0.25 to 1.0 g/cc; and a metal oxide supported on the silica support and including molybdenum (Mo), bismuth (Bi) and a dissimilar metal.

A commonly known ammoxidation catalyst for propylene may be prepared by a sol-gel method and provided in a secondary particle structure in which metal oxide nanoparticles and silica nanoparticles are aggregated (FIG. 1).

This may be a structure in which the metal oxide particles are evenly distributed inside and outside, but without internal pores, and the site capable of participating in the ammoxidation reaction of propylene may be limited to the outer surface portion.

In contrast, the catalyst of one embodiment may be prepared by an impregnation method and thus provided in a structure in which a metal oxide is supported on a silica support (FIG. 2).

For example, the silica support may be immersed in a metal precursor aqueous solution prepared to satisfy a desired stoichiometric molar ratio of the metal oxide, and the metal precursor aqueous solution may be impregnated in the silica support.

After that, when the solvent (i.e., water) is removed by a drying process, a metal precursor may remain on the pore wall of the silica support, and the metal precursor may be oxidized in a calcination process, thereby forming a film continuously coating the pore wall of the silica support.

The catalyst of one embodiment prepared as described above may have a narrower particle size distribution than a catalyst prepared with the same composition by the sol-gel method, and may have a smaller content of fine powder, even if a classification process is not performed as a post-treatment after preparation.

In particular, as the catalyst of one embodiment includes a silica support having a pore diameter and an apparent density within an appropriate range of 2 to 15 nm and 0.25 to 1.0 g/cc, respectively, it is possible to improve durability while further reducing the content of fine powder.

In addition, the catalyst of one embodiment may further increase a catalytic activity through a metal oxide including Mo and Bi, which are known to increase the activity of the ammoxidation reaction, as well as a metal that forms an active site at a suitable level for the ammoxidation reaction of propylene.

Thus, when using the catalyst of one embodiment, acrylonitrile can be obtained at a high yield without additional supply of the catalyst during the ammoxidation process of propylene performed in a fluidized bed reactor.

Hereinafter, the catalyst of one embodiment will be described in more detail.

Pore Diameter of Silica Support

The pore diameter of the silica support may refer to an average size of the pores in the particles, and may also refer to a Dp value at the maximum point of dVp/dDp in the dVp/dDp curve according to Dp obtained by the BJH calculation formula in the isothermal desorption curve of nitrogen gas under a temperature of liquid nitrogen. In the above, Dp may refer to the pore diameter of the particle and Vp may refer to the pore volume of the particle.

When the pore diameter of the silica support becomes excessively small to be less than 2 nm, the impregnation of the metal oxide into the pores of the silica support may not be uniformly performed, and thus the activity of the final catalyst may be lowered and the resulting non-impregnated metal oxide may be dissociated to form fine powder.

In contrast, when the pore diameter of the silica support becomes excessively large to be more than 15 nm, the final catalytic activity may be high, but the apparent density and durability may be lowered due to the large pore diameter, and thus the catalyst may be easily abraded and micronized in the fluidized bed reactor.

Accordingly, when using a silica support having an excessively small pore diameter of less than 2 nm, as well as a silica support having an excessively large pore diameter of more than 15 nm, it is necessary to continuously replenish the catalyst in the mass production of acrylonitrile, but there is still a limit to increasing the yield of acrylonitrile even after replenishing the catalyst.

Accordingly, in one embodiment of the present disclosure, the pore diameter of the silica support may be limited to 2 to 15 nm.

The pore diameter of the silica support may be controlled within the range of 2 to 30 nm, depending on desired physical properties for the final catalyst.

Specifically, when the composition and loading amount of the metal oxide are the same, the amount of the fine powder of the final catalyst may decrease and the particle size distribution may become uniform as the pore diameter of the silica support supporting the metal oxide decreases within the range of 2 to 15 nm.

For example, the pore diameter of the silica support may be controlled within the range of 15 nm or less, 14 nm or less, 13 nm or less, or 12 nm or less while being 2 nm or more.

Apparent Density of Silica Support

In general, the apparent density may refer to a value obtained by measuring the weight (W1) of a porous body contained in a container having a constant volume of 3 cc and dividing the weight by 3 cc, the constant volume of the container.

When the D50 particle diameter of the silica support is the same, the apparent density may tend to decrease as the pore diameter increases.

When the pore diameter of the silica support becomes large and thus the apparent density becomes excessively small to be less than 0.25 g/cc, the final catalytic activity may become high, but the apparent density and durability may become low, and thus the catalyst may be easily abraded and micronized in the fluidized bed reactor.

In contrast, when the pore diameter of the silica support becomes small and thus the apparent density becomes excessively large to be more than 1.0 g/cc, the impregnation of the metal oxide into the pores of the silica support may not be uniformly performed, and thus the activity of the final catalyst may be lowered and the resulting non-impregnated metal oxide may be dissociated to form fine powder.

Accordingly, even when using a silica support having an excessively small apparent density of less than 0.25 g/cc, as well as a silica support having an excessively large apparent density of more than 1.0 g/cc, it is necessary to continuously replenish a catalyst in the mass production of acrylonitrile, but there is still a limit to increasing the yield of acrylonitrile even after replenishing the catalyst.

The apparent density of the silica support may be controlled to 0.25 to 1.0 g/cc, depending on desired physical properties for the final catalyst.

Specifically, when the composition and loading amount of the metal oxide are the same, the amount of fine powder of the final catalyst may decrease as the apparent density of the silica support supporting the metal oxide increases within the range of 0.25 to 1.0 g/cc.

For example, the apparent density of the silica support may be 0.25 g/cc or more, 0.27 g/cc or more, 0.29 g/cc or more, or 0.3 g/cc or more while being 1.0 g/cc or less.

D50 Particle Diameter of Silica Support

The D50 particle diameter of the silica support may be 50 to 150 μm.

Specifically, the silica support may have the D50 particle diameter with a lower limit of 50 μm or more, 51 μm or more, 53 μm or more, or 55 μm or more, while having the D50 particle diameter with an upper limit of 150 μm or less, 110 μm or less, 90 μm or less, or 75 μm or less.

Ammonia Desorption Amount of Silica Support

In an initial stage of a catalytic reaction, a process in which reactants are chemically adsorbed on a catalyst surface is required, and the active site and surface area of the catalyst are directly related to an adsorption capacity and a resulting chemical reaction.

In addition, chemical adsorption on the catalyst surface may tend to increase with an increasing temperature, although the rate of adsorption is slower than that of physisorption.

In this regard, an ammonia temperature programmed desorption (NH$_3$-TPD) method, in which the strength of acid sites of the catalyst is measured according to the degree of temperature programmed desorption (TPD) of ammonia (NH$_3$), may be widely known.

For example, after pre-treatment at 400° C. for about one hour, NH$_3$ may be adsorbed with 5% NH$_3$/He (50 cc/min) at about 100° C. for one hour, and the physically adsorbed NH$_3$ may be removed while flowing He at the same temperature, after which the desorbed NH$_3$ may be measured while increasing the temperature up to 800° C.

The silica support may have an excellent adsorption capacity, since an ammonia (NH$_3$) desorption amount measured by the ammonia temperature programmed desorption (NH$_3$-TPD) method is 1.3 mmol/g or less, 1.2 mmol/g or less, 1.1 mmol/g or less, or 1.00 mmol/g or less (but, more than 0 mmol/g).

This may become a factor in reducing the amount of ammonia desorbed from the silica support and the catalyst including the same during the ammoxidation reaction of propylene, and improving the conversion rate of propylene, and the selectivity and yield of acrylonitrile.

Composition of Metal Oxide

Meanwhile, even if the catalyst has the same structure as the catalyst of one embodiment, a small amount of active sites or rather an excessively high density of active sites may be formed depending on the type and content of the components constituting the metal oxide.

In this regard, it is necessary to form an appropriate active site by adding a dissimilar metal rather than a metal oxide including only Mo and Bi as an active metal.

Specifically, in the catalyst of one embodiment, the type and content of the metal constituting the metal oxide may satisfy the Chemical Formula 1:

$$Mo_{12}Bi_bFe_bA_cB_dC_eO_x \qquad \text{[Chemical Formula 1]}$$

in the Chemical Formula 1,

A is at least one element of Ni, Mn, Co, Zn, Mg, Ca and Ba,

B is at least one element of Li, Na, K, Rb and Cs,

C is at least one element of Cr, W, B, Al, Ca and V, and a to e and x are each a fraction of an atom or atomic group,
wherein a is 0.1 to 5, b is 0.1 to 5, c is 0.01 to 10, d is 0.01 to 2, e is 0 to 10, and x is 24 to 48.

In particular, when the metal oxide is represented by the following Chemical Formula 1-1, the activity in the ammoxidation reaction of propylene may become higher due to the effect of increasing a conversion rate by increasing the movement rate of lattice oxygen of molybdenum and Fe, the effect of increasing the partial oxidation reaction properties of propylene by the formation of a composite oxide with molybdenum and Co, and a synergistic effect of the effect of increasing the AN selectivity by dispersing the active sites of the composite oxide containing molybdenum and K:

$$Mo_{12}Bi_aFe_bCo_cK_dO_x \qquad \text{[Chemical Formula 1-1]}$$

in the Chemical Formula 1-1, a to d and x are each a fraction of an atom or atomic group, wherein a is 0.1 to 5, specifically 01. to 2.0, b is 0.1 to 5, specifically 0.5 to 3.0, c is 0.01 to 10, specifically 1 to 10, d is 0.01 to 2, specifically 0.01 to 1.0, and x is 24 to 48, specifically 28 to 45.

Weight Ratio of Metal Oxide:Support

The catalyst of one embodiment may include the metal oxide and the silica support at a weight ratio of 15:85 to 35:65, specifically 20:80 to 35:65 (metal oxide: silica support).

Within the above range, the catalyst of one embodiment may have high selectivity of acrylonitrile with high activity.

Structure of Catalyst

The catalyst of one embodiment may have a structure including: a silica support containing a second pore; an inner coating layer continuously coating the wall surface of the second pore and including the metal oxide represented by the Chemical Formula 1; and a first pore positioned inside the second pore and occupying an empty space excluding the inner coating layer.

Herein, a diameter of the second pore may be 2 to 15 nm, and the first pore may be determined according to the amount of the metal oxide supported in the second pore.

In terms of such a supported structure, the catalyst may have a small content of fine powder, excellent durability, and high activity compared to a catalyst prepared by a sol-gel method.

Accordingly, when using the catalyst of one embodiment, acrylonitrile can be obtained at a high yield without additional supply of the catalyst during the ammoxidation process of propylene in a fluidized bed reactor.

Specifically, the catalyst of one embodiment may have an egg-shell structure.

To that end, the silica support may include: a non-porous core portion; and a porous shell portion located on the surface of the non-porous core and including a second pore having a diameter of 2 to 30 nm.

Specifically, the porous shell may include a concave portion and a convex portion of the surface, in which the concave portion is formed by opening the second pores to the surface of the porous shell.

Accordingly, the catalyst of one embodiment may have a structure including: a coating layer continuously coating concave and convex portions of the porous shell and including a metal oxide represented by the Chemical Formula 1; and a first pore occupying an empty space excluding the coating layer in the concave portion of the silica support.

D50 Particle Diameter of Final Catalyst and Uniformity of Particle Size Distribution The catalyst of one embodiment may have a uniform particle size distribution compared to D50 and a less content of fine powder while the metal oxide is supported on the silica support.

Specifically, the catalyst of one embodiment may have a D50 particle diameter of 30 to 200 µm and exhibit a narrow particle size distribution, since a ratio of [difference between D90 particle diameter and D10 particle diameter] to the D50 particle diameter is 2.0 or less.

More specifically, the catalyst of one embodiment may have the D50 particle diameter with a lower limit of 30 µm or more, 35 µm or more, 40 µm or more, or 45 µm or more, while having the D50 particle diameter with an upper limit of 200 µm or less, 190 µm or less, 180 µm or less, 170 µm or less, 160 µm or less, or 150 µm or less.

In addition, the catalyst of one embodiment may exhibit a narrow particle size distribution, since a ratio of [difference between D90 particle diameter and D10 particle diameter] to the D50 particle diameter is less than 2.0, 1.7 or less, 1.5 or less, 1.3 or less, or 1.0 or less.

In other words, the uniformity of the particle size distribution exhibited by the catalyst of one embodiment may be supported by the fact that the D10 particle diameter and the D90 particle diameter compared to the D50 particle diameter satisfy the relationship of Equation 1-1 below:

$$(D90-D10)/D50 \leq 2.0 \qquad \text{[Equation 1]}$$

$$(D90-D10)/D50 \qquad \text{[Equation 1-1]}$$

Attrition Loss Amount of Catalyst

The attrition of particles may refer to a phenomenon in which solid particles are decomposed through mechanical and chemical processes. Particle attrition may be classified into two types: abrasion and fragmentation, both of which may occur together.

In particular, in a fluidized bed process, the catalyst particles may be abraded and micronized, and it is necessary to continuously replenish the catalyst by the amount of catalyst particles attrited, which may affect the economic feasibility of the entire process.

ASTM9797-00 method is known as a standard for measuring the attrition of particles. This may correspond to a method of measuring wear resistance (attrition loss) using the following equation by filling a vertical inner tube having an inner diameter of 35 mm and a height of 710 mm with 50 g of catalyst (W0), flowing $N_2$ gas at 10 L/min, and measuring the amount (W) of the catalyst collected in a fine filter after five hours.

$$\text{Wear resistance (attrition loss) (\%)} = (W0)/W \times 100$$

The catalyst of one embodiment may have a very small amount of loss and excellent wear resistance, since the wear resistance (attrition loss) measured according to the ASTM9797-00 method is 10% or less, 9% or less, 8% or less, 7% or less, 6% or less, or 5% or less.

Thus, the catalyst of one embodiment exhibits excellent wear resistance compared to the catalyst prepared according to the sol-gel method, and may prepare acrylonitrile at a higher yield without additional supply of the catalyst during the ammoxidation reaction of propylene in a fluidized bed reactor.

Manufacturing Method of an Ammoxidation Catalyst for Propylene

In another embodiment of the present disclosure, there is provided a manufacturing method of the catalyst of one embodiment described above by using an impregnation method.

As briefly described above, the catalyst of one embodiment may be manufactured through a series of processes of supporting a metal precursor aqueous solution on the silica support through an impregnation method, followed by drying and calcining.

More specifically, there is provided a manufacturing method of the catalyst of one embodiment including the steps of:

preparing a first precursor aqueous solution containing a Mo precursor;

preparing a second precursor aqueous solution containing a Bi precursor and a dissimilar metal precursor;

supporting a mixture of the first and second precursor aqueous solutions on a silica support containing a pore having a diameter of 2 to 15 nm and an apparent density of 0.25 to 1.0 g/cc;

drying the silica support on which the mixture of the first and second precursor aqueous solutions is supported; and calcining the dried material.

Hereinafter, a description overlapping with the above-described content will be omitted, and a process of manufacturing the catalyst of one embodiment will be described in detail.

Process for Preparing a First Precursor Aqueous Solution

In the step of preparing the first precursor aqueous solution, an additive including citric acid, oxalic acid or a mixture thereof may be added.

The additive may function as a strength regulator in a catalyst manufacturing process using co-precipitation and spray-drying, but may serve to make the first precursor aqueous solution transparent in one embodiment.

When the additive is added, a weight ratio of the molybdenum precursor and the additive may satisfy 1:0.1 to 1:1, specifically 1:0.2 to 1:0.7, and solubility of the molybdenum precursor may increase within the range, but is not limited thereto.

Process for Preparing a Second Precursor Aqueous Solution

A second precursor aqueous solution containing the remaining metal precursors except for the Mo precursor contained in the first precursor aqueous solution may be prepared.

Specifically, the step of preparing the second precursor aqueous solution may be a step of preparing a second precursor aqueous solution including a Bi precursor, a Fe precursor, an A precursor (A=at least one element of Ni, Mn, Co, Zn, Mg, Ca and Ba), and a B precursor (B=at least one element of Li, Na, K, Rb and Cs).

More specifically, in the step of preparing the second precursor aqueous solution, the type of the metal precursor excluding the Mo precursor may be selected in consideration of the final desired metal oxide composition in the catalyst.

For example, in consideration of the metal oxide composition satisfying the Chemical Formula 1-1 mentioned above, a second precursor aqueous solution including a Bi precursor, a Fe precursor, a Co precursor and a K precursor may be prepared.

Herein, it is also possible to prepare a second precursor aqueous solution further including a C precursor (at least one element of Cr, W, B, Al, Ca and V).

Mixture of First and Second Precursor Aqueous Solutions

The processes of preparing the first and second precursor aqueous solutions are independent of each other, and the preparation order is not limited.

However, the mixture of the first and second precursor aqueous solutions may be prepared so that a molar ratio of the metal satisfies the following stoichiometric molar ratio of Chemical Formula 1:

$$Mo_{12}Bi_aFe_bA_cB_dC_eO_x \qquad \text{[Chemical Formula 1]}$$

in the Chemical Formula 1,

A is at least one element of Ni, Mn, Co, Zn, Mg, Ca and Ba,

B is at least one element of Li, Na, K, Rb and Cs,

C is at least one element of Cr, W, B, Al, Ca and V, and a to e and x are a fraction of an atom or atomic group, wherein a is 0.1 to 5, b is 0.1 to 5, c is 0.01 to 10, d is 0.01 to 2, e is 0 to 10, and x is 24 to 48.

Process of Supporting the Mixture of First and Second Precursor Aqueous Solutions on Support The first and second precursor aqueous solutions may be mixed, and then supported on a silica support.

Herein, the silica support containing the aforementioned second pore may be added to the mixture of the first and second precursor aqueous solutions, so that the mixture of the first and second precursor aqueous solutions may be supported in the pore of the silica support.

Specifically, the D50 size of the silica support per se on which the metal oxide is not supported may be 20 to 400 µm.

Process of Drying the Support on Which the Mixture of First and Second Precursor Aqueous Solutions is Supported The step of drying the silica support on which the mixture of the first and second precursor aqueous solutions is supported may include the steps of: primarily vacuum-drying the silica support on which the mixture of the first and second precursor aqueous solutions is supported at 120 to 160 mbar; and secondarily vacuum-drying the primarily vacuum-dried material at 30 to 50 mbar so as to obtain the silica support on which the mixture of the first and second precursor aqueous solutions is supported.

Specifically, the primary vacuum-drying may be performed at 60 to 80° C. for 1 to 2 hours, and the secondary vacuum-drying may be performed at 80 to 100° C. for 15 to 45 minutes. Thus, the solvent (i.e., water) may be removed and only the first and second precursors may remain on the pore wall surface of the silica support.

Although the material for which the secondary vacuum-drying has been completed can be immediately calcined, the material may be tertiarily dried at normal pressure so as to effectively remove even the solvent (i.e., water) remaining after the secondary vacuum-drying.

Specifically, the tertiary drying may be performed at 100 to 120° C. for 20 to 30 hours.

However, this is only an example, and may not be particularly limited as long as the process is performed under the drying conditions in which the solvent (i.e., water) is removed to obtain the support on which the first and second precursors are supported.

Final Calcination Process

Finally, the dried material, that is, the support on which the first and second precursors are supported, is calcined within a temperature range of 500 to 700° C. for 2 to 5 hours so as to finally obtain a catalyst.

However, each of the drying and calcining conditions is only an example, and is sufficient as long as the solvent may be sufficiently removed from the internal pores of the support and the metal precursor can be oxidized.

Ammoxidation Method of Propylene

In another embodiment of the present disclosure, there is provided an ammoxidation method of propylene including the step of reacting propylene and ammonia in the presence of the catalyst of one embodiment described above in a reactor.

The catalyst of one embodiment may have stability at high temperatures along with high activity, and may be used for ammoxidation reaction of propylene to increase the conversion rate of propylene, and the selectivity and yield of acrylonitrile.

For matters other than the catalyst of one embodiment, reference may be made to matters generally known in the art and thus further detailed description thereof will be omitted.

Hereinafter, the embodiments of the present disclosure will be described in more detail through the following embodiments. However, the following embodiments are provided only for the purpose of illustrating the present disclosure, and thus the present disclosure is not limited thereto.

EXAMPLES

Example 1

(1) Process of Preparing a Precursor Solution 10.59 g of Mo precursor ((NH$_4$)$_6$Mo$_7$O$_{24}$) and 5.3 g of citric acid were added in distilled water, and mixed to prepare a Mo precursor solution.

Independently, 1.82 g of Bi precursor (Bi(NO$_3$)$_3$·5H$_2$O), 9.49 g of Co precursor (Co(NO$_3$)$_2$·6H$_2$O), 2.99 g of Fe precursor (Fe(NO$_3$)$_2$·9H$_2$O), and 0.35 g of K precursor (KNO$_3$) were added in distilled water, and 2.29 g of nitric acid (HNO$_3$) was added thereto and mixed so as to prepare a mixed solution of Bi, Fe, Co and K precursors.

The Mo precursor solution; and the mixed solution of Bi, Fe, Co and K precursors were mixed to complete a mixed solution of Mo, Bi, Fe, Co and K precursors.

In the mixed solution of precursors, the total amount of distilled water is 45.74 g.

(2) Process of Supporting a Precursor Solution in Silica Support (Using Impregnation Method)

A silica particle containing pores with an average diameter of 12 nm, an apparent density of 0.32 g/cc and a D50 particle diameter of 70 μm (SiO$_2$, D60-120A(N), AGC Si-Tech Co., Ltd.) was used as a support.

18.30 g of the silica support was added in the mixed solution of Mo, Bi, Fe, Co and K precursors, and sequentially stirred at room temperature and at 80° C. for 2 hours, respectively, so that the mixed solution of Mo, Bi, The Fe, Ni, Co and K precursors was sufficiently supported in the pores of the silica support.

(3) Process of Drying and Calcining the Silica Support with Precursor Solution Supported Thereon After that, the silica support on which the mixed solution of Bi, Fe, Co and K precursors is supported was recovered and put into a rotary vacuum dryer. Thereafter, it was primarily vacuum-dried for 1 hour and 40 minutes at a pressure of 140 mbar and a temperature of 70° C., and then secondarily vacuum-dried for 30 minutes at a pressure of 40 mbar and a temperature of 90° C.

The material in which the secondary vacuum-drying has been completed was recovered, put into an oven, tertiarily dried for 24 hours at a normal pressure and a temperature of 110° C., and heat-treated for 3 hours in a box kiln under an air atmosphere while maintaining a temperature of 580° C. so as to finally obtain the catalyst of Example 1.

(4) Ammoxidation Process of Propylene

In a tubular reactor having an inner diameter of ⅜ inch, 0.05 g of quartz wool was filled for activation of the catalyst and 0.2 g of the catalyst of Example 1 was filled in the reactor.

The internal pressure of the reactor filled with the quartz wool and the catalyst was maintained at a normal pressure (1 atm) and nitrogen and ammonia gas were flowed as a pre-treatment process while increasing an internal temperature of the reactor at a temperature increase rate of 10° C./min. Accordingly, after the internal temperature of the reactor reached 400° C. at which the ammoxidation reaction is possible, it was maintained under a reducing gas atmosphere for 15 minutes to ensure sufficient pre-treatment.

Air was supplied along with propylene and ammonia, which are reactants, to the reactor in which the pre-treatment was completed, and the ammoxidation process of propylene was performed. At this time, while the feed amount of reactants was set to reach a volume ratio of propylene:ammonia:air=0.8:1.2:8, the total weight hourly space velocity (WHSV) of propylene, ammonia and air was set to 1.54 h$^{-1}$.

After completion of the ammoxidation reaction, the resulting product was recovered and analyzed by using various equipment in order to confirm whether acrylonitrile was well produced.

The analysis method, analysis result, and the like will be described in detail in Experimental Examples to be described later.

Examples 2 to 7

Each catalyst of Examples 2 to 7 was prepared in the same manner as in Example 1, except for preparing a precursor solution according to the composition shown in Table 1 below and using the silica support shown in Table 2 below.

In addition, the ammoxidation process of propylene was performed by using each catalyst of Examples 2 to 7 instead of the catalyst of Example 1, and then the resulting product was recovered and analyzed in the same manner as in Example 1.

Comparative Example 1

(1) Process of Preparing a Catalyst (Using Spray-Drying After Co-Precipitation)

First, 10.59 g of Mo precursor ((NH$_4$)$_6$Mo$_7$O$_{24}$) and 5.3 g of citric acid were added in distilled water, and mixed to prepare a Mo precursor solution.

Independently, 1.82 g of Bi precursor (Bi (NO$_3$)$_3$·5H$_2$O), 9.49 g of Co precursor (Co(NO$_3$)$_2$·6H$_2$O), 2.99 g of Fe precursor (Fe(NO$_3$)$_2$·9H$_2$O), and 0.35 g of K precursor (KNOB) were added in distilled water, and 1.13 g of nitric acid (HNO$_3$) was added thereto and mixed so as to prepare a mixed solution of Bi, Fe, Co and K precursors.

After the Mo precursor solution; and the mixed solution of Bi, Fe, Co and K precursors were mixed, 22.53 g of silica sol (LUDOX AS 40, solid content: 40%, Grace) was added thereto and stirred, and then spray-dried under the condition of 120° C. (inlet) and 230° C. (outlet) by using a disk-type spray dryer.

The resulting powder was calcined at 580° C. for 3 hours to finally obtain the catalyst of Comparative Example 1.

(3) Ammoxidation Process of Propylene

The ammoxidation process of propylene was performed in the same manner as in Example 1, except for using the catalyst of Comparative Example 1 instead of the catalyst of Example 1.

After completion of the ammoxidation reaction of Comparative Example 1, the resulting product was recovered and analyzed in the same manner as in Example 1.

Comparative Examples 2 and 3

Each catalyst of Comparative Examples 2 and 3 was prepared in the same manner as in Example 1, except for preparing a precursor solution according to the composition shown in Table 1 below and using the silica support shown in Table 2 below.

In addition, the ammoxidation process of propylene was performed by using each catalyst of Comparative Examples 2 and 3 instead of the catalyst of Example 1, and then the resulting product was recovered and analyzed in the same manner as in Example 1.

Comparative Example 4

A catalyst of Comparative Example 4 was prepared in the same manner as in Comparative Example 1, except for preparing a precursor solution according to the composition shown in Table 1 below and using the silica support shown in Table 2 below.

In addition, the ammoxidation process of propylene was performed by using the catalyst of Comparative Example 4 instead of the catalyst of Comparative Example 1, and then the resulting product was recovered and analyzed in the same manner as in Comparative Example 1.

Comparative Example 5

A catalyst of Comparative Example 5 was prepared in the same manner as in Example 1, except for using the silica support shown in Table 1 below and performing the supporting process considering the composition of the metal oxide shown in Table 2 below and the mixing ratio thereof with the silica support.

In addition, the ammoxidation process of propylene was performed by using the catalyst of Comparative Example 5 instead of the catalyst of Example 1, and then the resulting product was recovered and analyzed in the same manner as in Example 1.

TABLE 1

| Category | Mo precursor solution | | Dissimilar metal precursor solution | | | | | | | Distilled water | SiO$_2$ |
|---|---|---|---|---|---|---|---|---|---|---|---|
| | Citric acid | Mo | Bi | Fe | Co | Ni | K | HNO$_3$ | H$_3$PO$_4$ | | |
| Ex. 1 | 5.30 | 10.59 | 1.82 | 2.99 | 9.49 | 0.00 | 0.35 | 2.29 | 0 | 45.74 | 18.30 |
| Ex. 2 | 5.30 | 10.59 | 1.82 | 2.99 | 9.49 | 0.00 | 0.35 | 2.29 | 0 | 45.74 | 18.30 |
| Ex. 3 | 5.30 | 10.59 | 1.82 | 2.99 | 9.49 | 0.00 | 0.35 | 3.38 | 0 | 67.59 | 27.04 |
| Ex. 4 | 5.30 | 10.59 | 1.82 | 2.99 | 9.49 | 0.00 | 0.35 | 4.51 | 0 | 90.12 | 36.05 |
| Ex. 5 | 5.30 | 10.59 | 2.91 | 2.02 | 6.40 | 0.00 | 0.02 | 2.18 | 0 | 43.61 | 17.45 |
| Ex. 6 | 5.30 | 10.59 | 2.18 | 3.03 | 9.46 | 1.60 | 0.05 | 2.38 | 0 | 47.58 | 19.03 |
| Ex. 7 | 5.30 | 10.59 | 2.43 | 6.06 | 6.55 | 3.64 | 0.05 | 2.47 | 0 | 49.33 | 19.73 |
| Comp. Ex. 1 | 5.30 | 10.59 | 1.82 | 2.99 | 9.49 | 0.00 | 0.35 | 1.13 | 0 | 22.53 | 22.53 |
| Comp. Ex. 2 | 5.30 | 10.59 | 1.82 | 2.99 | 9.49 | 0.00 | 0.35 | 2.29 | 0 | 45.74 | 18.30 |
| Comp. Ex. 3 | 5.30 | 10.59 | 1.82 | 2.99 | 9.49 | 0.00 | 0.35 | 2.29 | 0 | 45.74 | 18.30 |
| Comp. Ex. 4 | 5.30 | 10.59 | 2.43 | 6.06 | 6.55 | 3.64 | 0.05 | 1.20 | 0.25 | 24.49 | 24.49 |
| Comp. Ex. 5 | 4.41 | 8.83 | 48.51 | 0.00 | 0.00 | 0.00 | 0.00 | 1.20 | 0 | 52.17 | 52.17 |

In above Table 1, Mo is $(NH_4)_6Mo_7O_{24}$, Bi is $Bi(NO_3)_3 \cdot 5H_2O$, Fe is $Fe(NO_3)_2 \cdot 9H_2O$, Co is $Co(NO_3)_2 \cdot 6H_2O$, Ni is $Ni(NO_3)_2 \cdot 6H_2O$, and K is $KNO_3$.

sample in the container was measured and divided by the volume of the container so as to obtain an apparent density of the sample.

TABLE 2

| Category | Prep. method | Catalyst composition | | Support Product name |
|---|---|---|---|---|
| | | Content and composition of active materials (metal oxide) | Content of support | |
| Ex. 1 | Impreg. method | 33 wt % $(Mo_{12}Bi_{0.75}Fe_{1.48}Co_{6.52}K_{0.7}O_x)$ | 67 wt % | D60-120A |
| Ex. 2 | Impreg. method | 33 wt % $(Mo_{12}B_{i0.75}Fe_{1.48}Co_{6.52}K_{0.7}O_x)$ | 67 wt % | Silica gel 60 (Merk) |
| Ex. 3 | Impreg. method | 25 wt % $(Mo_{12}Bi_{0.75}Fe_{1.48}Co_{6.52}K_{0.7}O_x)$ | 75 wt % | D60-60A(N) |
| Ex. 4 | Impreg. method | 20 wt % $(Mo_{12}B_{i0.75}Fe_{1.48}Co_{6.52}K_{0.7}O_x)$ | 80 wt % | D60-60A(N) |
| Ex. 5 | Impreg. method | 33 wt % $(Mo_{12}Bi_{1.2}Fe_{1.0}Co_{4.4}K_{0.03}O_x)$ | 67 wt % | D60-60A(N) |
| Ex. 6 | Impregnation method | 33 wt % $(Mo_{12}Bi_{0.9}Fe_{1.5}Co_{6.5}Ni_{1.1}K_{0.1}O_x)$ | 67 wt % | D60-60A(N) |
| Ex. 7 | Impreg. method | 33 wt % $(Mo_{12}Bi_{1.0}Fe_{3.0}Co_{4.5}Ni_{2.5}K_{0.1}O_x)$ | 67 wt % | D60-60A(N) |
| Comp. Ex. 1 | Sol-gel method | 50 wt % $(Mo_{12}Bi_{0.75}Fe_{1.48}Co_{6.52}K_{0.7}O_x)$ | 50 wt % | LUDOX_AS40 (Grace) |
| Comp. Ex. 2 | Impreg. method | 33 wt % $(Mo_{12}Bi_{0.75}Fe_{1.48}Co_{6.52}K_{0.7}O_x)$ | 67 wt % | Q-23(Wakogel) |
| Comp. Ex. 3 | Impreg. method | 33 wt % $(Mo_{12}Bi_{0.75}Fe_{1.48}Co_{6.52}K_{0.7}O_x)$ | 67 wt % | SP948 (Grace) |
| Comp. Ex. 4 | Sol-gel method | 33 wt % $(Mo_{12}Bi_{1.0}Fe_{3.0}Co_{4.5}Ni_{2.5}K_{0.1}P_{0.5}O_x)$ | 67 wt % | LUDOX_AS40 (Grace) |
| Comp. Ex. 5 | Impreg. method | 33 wt % $(Bi2O_3 \cdot MoO_3)$ | 67 wt % | D60-60A(N) |

Experimental Example 1: Analysis of Silica Support

Each silica support used in Examples and Comparative Examples was analyzed according to the following analysis method and the analysis results thereof are shown in Table 3 below:

Apparent density: A sample was added into a 3 cm$^3$ (cc) container in a free-falling method, after which a certain amount of the sample was added or subtracted so that the surface of the sample in the container is in a straight line with the surface of the container. Then, the weight of the Average diameter of pores: By using a BET specific surface area measuring device (manufactured by BEL Japan with the device name: BELSORP_Mini), a pore size was measured with the BJH equation using an adsorption amount measured up to relative pressure (P/P0) 1 and a desorption amount measured up to 0.03 at a liquid nitrogen temperature (77 K).

D50 particle diameter: Dv may be measured by using a laser diffraction method. Specifically, each silica support of Examples and Comparative Examples was introduced into a particle size measuring device (Microtrac, Blue wave) using a laser diffraction method, and then a particle size distribution was obtained by measuring a difference in diffraction patterns according to particle sizes when the particles pass through the laser beam. In the measuring device, the value of D50 was obtained by calculating a particle diameter at a point of reaching 50% of the cumulative volume distribution according to particle diameters.

Ammonia ($NH_3$) desorption amount: About 0.1 g of the catalyst was filled into a U-shaped quartz tube, after which a U-shaped reactor was connected to the device, and then a temperature was raised from room temperature to about 400° C. at a temperature increase rate of 10° C./min by using helium gas (50 cc/min), followed by pre-treatment while maintaining at 400° C. for about 1 hour. This was to remove organic matters remaining in the catalyst.

After completion of the pre-treatment, $NH_3$ was adsorbed with 5% $NH_3$/He (50 cc/min) at about 100° C. for 1 hour. While flowing He at the same temperature, the physically adsorbed $NH_3$ was removed and the desorbed $NH_3$ was measured while raising a temperature up to 800° C.

active materials (metal oxide), the apparent density of the support and the average pore diameter are also shown in Table 4 below:

Measurement of D10, D50 and D90: Dv may be measured by using a laser diffraction method. Specifically, each catalyst of Examples and Comparative Examples was introduced into a particle size measuring device (Microtrac, Blue wave) using a laser diffraction method, and then a particle size distribution was obtained by measuring a difference in diffraction patterns according to particle sizes when the particles pass through the laser beam. In the measuring device, the particle diameter was calculated at the point of reaching 10%, 50% and 90% of the cumulative volume distribution according to particle sizes, thereby obtaining the values of D10, D50 and D90 and also outputting the particle size distribution (value of (D90-D10)/D50).

Wear resistance (attrition loss): Based on ASTM9797-00 method, wear resistance (attrition loss) was measured with

TABLE 3

Physical properties of support

| Category | Product name | Apparent density | Average diameter of pores | D50 particle diameter | Ammonia desorption amount |
|---|---|---|---|---|---|
| Ex. 1 | D60-120A(N) | 0.32 g/cc | 12 nm | 70 μm | 0.98 mmol/g |
| Ex. 2 | Silica gel 60 (Merk) | 0.62 g/cc | 4.8 nm | 56 μm | 0.86 mmol/g |
| Ex. 3 | D60-60A(N) | 0.49 g/cc | 5.8 nm | 61 μm | 1.00 mmol/g |
| Ex. 4 | D60-60A(N) | 0.49 g/cc | 5.8 nm | 61 μm | 1.00 mmol/g |
| Ex. 5 | D60-60A(N) | 0.49 g/cc | 5.8 nm | 61 μm | 1.00 mmol/g |
| Ex. 6 | D60-60A(N) | 0.49 g/cc | 5.8 nm | 61 μm | 1.00 mmol/g |
| Ex. 7 | D60-60A(N) | 0.49 g/cc | 5.8 nm | 61 μm | 1.00 mmol/g |
| Comp. Ex. 1 | LUDOX_AS40 (Grace) | — | <1 nm | 20 nm | — |
| Comp. Ex. 2 | Q-23(Wakogel) | 1.1 g/cc | 1.5 nm | 70 μm | 1.43 mmol/g |
| Comp. Ex. 3 | SP948(Grace) | 0.2 g/cc | 16 nm | 55 μm | 0.72 mmol/g |
| Comp. Ex. 4 | LUDOX_AS40 (Grace) | 0.49 g/cc | 5.8 nm | 20 nm | — |
| Comp. Ex. 5 | D60-60A(N) | 0.49 g/cc | 5.8 nm | 61 μm | 1.00 mmol/g |

Experimental Example 2: Catalyst Analysis

Each catalyst of the Examples and the Comparative Examples was analyzed according to the following analysis method and the analysis results thereof are shown in Table 4 below. For reference, the content and composition of the equation below by filling 50 g of the catalyst (W0) into a vertical inner tube having an inner diameter of 35 mm and a height of 710 mm, flowing $N_2$ gas at 10 L/min, and measuring the weight (W) of the catalyst collected in a fine filter after 5 hours.

Wear resistance (attrition loss) (%)=(W0)/W×100

TABLE 4

| | | | | Support | | Physical properties of catalyst | |
| Categ. | Prep. method | Content and composition of active materials (metal oxide) | | Apparent density | Average diameter of pores | Catalyst (D90 − D10)/D50 | Attrition loss (ASTM5 hrs) |
|---|---|---|---|---|---|---|---|
| Ex. 1 | Impreg. method | 33 wt % ($Mo_{12}Bi_{0.75}Fe_{1.48}Co_{6.52}K_{0.7}O_x$) | | 0.32 g/cc | 12 nm | 0.82 | 2.5% |
| Ex. 2 | Impreg. method | 33 wt % ($Mo_{12}B_{i0.75}Fe_{1.48}Co_{6.52}K_{0.7}O_x$) | | 0.62 g/cc | 4.8 nm | 0.53 | 0.7% |
| Ex. 3 | Impreg. method | 25 wt % ($Mo_{12}Bi_{0.75}Fe_{1.48}Co_{6.52}K_{0.7}O_x$) | | 0.49 g/cc | 5.8 nm | 0.62 | 1.5% |
| Ex. 4 | Impreg. method | 20 wt % ($Mo_{12}B_{i0.75}Fe_{1.48}Co_{6.52}K_{0.7}O_x$) | | 0.49 g/cc | 5.8 nm | 0.58 | 1.4% |
| Ex. 5 | Impreg. method | 33 wt % ($Mo_{12}Bi_{1.2}Fe_{1.0}Co_{4.4}K_{0.03}O_x$) | | 0.49 g/cc | 5.8 nm | 0.61 | 2.8% |

TABLE 4-continued

| | | | | Support | Physical properties of catalyst | |
| | | | | | | |
| Categ. | Prep. method | Content and composition of active materials (metal oxide) | Apparent density | Average diameter of pores | Catalyst (D90 − D10)/D50 | Attrition loss (ASTM5 hrs) |
|---|---|---|---|---|---|---|
| Ex. 6 | Impreg. method | 33 wt %($Mo_{12}Bi_{0.9}Fe_{1.5}Co_{6.5}Ni_{1.1}K_{0.1}O_x$) | 0.49 g/cc | 5.8 nm | 0.61 | 2.8% |
| Ex. 7 | Impreg. method | 33 wt %($Mo_{12}Bi_{1.0}Fe_{3.0}Co_{4.5}Ni_{2.5}K_{0.1}O_x$) | 0.49 g/cc | 5.8 nm | 0.60 | 4.6% |
| Comp. Ex. 1 | Sol-gel method | 50 wt %($Mo_{12}Bi_{0.75}Fe_{1.48}Co_{6.52}K_{0.7}O_x$) | — | <1 nm | 2.3 | 10.2% |
| Comp. Ex. 2 | Impreg. method | 33 wt %($Mo_{12}Bi_{0.75}Fe_{1.48}Co_{6.52}K_{0.7}O_x$) | 1.1 g/cc | 1.5 nm | 4.2 | 5.2% |
| Comp. Ex. 3 | Impreg. method | 33 wt %($Mo_{12}Bi_{0.75}Fe_{1.48}Co_{6.52}K_{0.7}O_x$) | 0.2 g/cc | 16 nm | 0.86 | 18% |
| Comp. Ex. 4 | Sol-gel method | 33 wt %($Mo_{12}Bi_{1.0}Fe_{3.0}Co_{4.5}Ni_{2.5}K_{0.1}P_{0.5}O_x$) | 0.49 g/cc | 5.8 nm | 3.2 | 14.3% |
| Comp. Ex. 5 | Impreg. method | 33 wt %($Bi_2O_3{\cdot}MoO_3$) | 0.49 g/cc | 5.8 nm | 4.8 | 23% |

In above Table 4, the catalysts of Examples 1 to 7 showed a narrower particle size distribution and a smaller wear rate compared to the catalysts of Comparative Examples 1 to 5.

In particular, in relation to the catalysts of Comparative Examples 1 and 4, prepared by the sol-gel method, the impregnation method used to prepare the catalysts of Examples 1 to 7 may be an advantageous method for forming a structure in which a metal oxide is supported on a silica support so as to prepare a catalyst having a narrow particle size distribution and excellent wear resistance.

However, the catalysts of Comparative Examples 2 and 3 were prepared by the impregnation method, but showed a wide particle size distribution and high attrition loss.

The catalyst of Comparative Example 2 used a silica support having a small pore diameter of 1.5 nm, a large amount of metal oxides were not impregnated into the small pores of the silica support in the supporting process, and a large amount of fine powder formed by the non-impregnated metal oxide was included to obtain a wide particle size distribution and poor wear resistance.

Meanwhile, each catalyst of Comparative Example 3 was easily micronized with low apparent density and durability by using a silica support having a large pore diameter of 16 nm.

The catalyst of Comparative Example 5 was also prepared by the impregnation method, but showed a wide particle size distribution and high attrition loss.

The catalyst of Comparative Example 5 used a silica support having a pore diameter and an apparent density within an appropriate range, respectively, but showed a wide particle size distribution and poor wear resistance under the influence of a metal oxide containing only Mo and Bi as active metals.

In contrast, the catalysts of Examples 1 to 7 showed a narrow particle size distribution and excellent wear resistance as a result of using a silica support having a pore diameter and an apparent density within an appropriate range of 2 to 15 nm and 0.3 to 1.0 g/cc, respectively, and supporting a metal oxide further containing Mo and Bi as well as active metal components such as Fe, Co, K, etc., on the silica support.

In particular, the catalysts of Examples 1 to 7 showed a uniform particle size distribution with (D90-D10)/D50 of 2 or less, specifically 0.85 or less, and thus showed attrition loss of 10% or less, specifically 5% or less according to the ASTM9797-00 method.

Experimental Example 3: Analysis of Ammoxidation Product of Propylene

Each ammoxidation product of Examples and Comparative Examples was analyzed by using chromatography (gas chromatography manufactured by Agilent with the machine name: HP 6890 N) equipped with a flame ionization detector (FID) and a thermal conductivity detector (TCD).

Specifically, products such as ethylene, hydrogen cyanide, acetaldehyde, acetonitrile, acrylonitrile, etc., were analyzed by FID, and gas products such as $NH_3$, $O_2$, CO, $CO_2$ and unreacted propylene were analyzed by TCD to determine the number of moles of reacted propylene and the number of moles of ammoxidation products in Examples and Comparative Examples, respectively.

By applying the number of moles of propylene supplied along with the analysis results to the following Equations 1, 2 and 3, the conversion rate of propylene, and the selectivity and yield of acrylonitrile, which is an ammoxidation product of propylene, were calculated and the resulting values are shown in Table 5.

For reference, the content and composition of active materials (metal oxide), the apparent density of the support and the average pore diameter are also shown in Table 5 below:

Conversion rate of propylene (%)=100*(Number of moles of ammoxidation of reacted propylene)/ (Number of moles of supplied propylene)          [Equation 1]

Selectivity of acrylonitrile (%)=100*(Number of moles of generated acrylonitrile)/(Number of moles of reacted propylene)          [Equation 2]

Yield of acrylonitrile (%)=100*(Number of moles of generated acrylonitrile)/(Number of moles of supplied propylene)          [Equation 3]

TABLE 5

| Categ. | Prep. method | Content and composition of active materials (metal oxide) | Support | | Analysis results of ammoxidation product of propylene | | |
|---|---|---|---|---|---|---|---|
| | | | Apparent density | Av. diam. of pores | Convers. rate of propylene (%) | Selectivity of acrylonitrile (%) | Yield of acrylonitrile (%) |
| Ex. 1 | Impregnation method | 33 wt % $(Mo_{12}Bi_{0.75}Fe_{1.48}Co_{6.52}K_{0.7}O_x)$ | 0.32 g/cc | 12 nm | 64 | 70 | 45 |
| Ex. 2 | Impregnation method | 33 wt % $(Mo_{12}Bi_{0.75}Fe_{1.48}Co_{6.52}K_{0.7}O_x)$ | 0.62 g/cc | 4.8 nm | 62 | 68 | 42 |
| Ex. 3 | Impregnation method | 25 wt % $(Mo_{12}Bi_{0.75}Fe_{1.48}Co_{6.52}K_{0.7}O_x)$ | 0.49 g/cc | 5.8 nm | 58 | 69 | 40 |
| Ex. 4 | Impregnation method | 20 wt % $(Mo_{12}Bi_{0.75}Fe_{1.48}Co_{6.52}K_{0.7}O_x)$ | 0.49 g/cc | 5.8 nm | 57 | 68 | 39 |
| Ex. 5 | Impregnation method | 33 wt % $(Mo_{12}Bi_{1.2}Fe_{1.0}Co_{4.4}K_{0.03}O_x)$ | 0.49 g/cc | 5.8 nm | 67 | 85 | 57 |
| Ex. 6 | Impregnation method | 33 wt % $(Mo_{12}Bi_{0.9}Fe_{1.5}Co_{6.5}Ni_{1.1}K_{0.1}O_x)$ | 0.49 g/cc | 5.8 nm | 67 | 85 | 57 |
| Ex. 7 | Impregnation method | 33 wt % $(Mo_{12}Bi_{1.0}Fe_{3.0}Co_{4.5}Ni_{2.5}K_{0.1}O_x)$ | 0.49 g/cc | 5.8 nm | 42 | 88 | 37 |
| Comp. Ex. 1 | Sol-gel method | 50 wt % $(Mo_{12}Bi_{0.75}Fe_{1.48}Co_{6.52}K_{0.7}O_x)$ | — | <1 nm | 14 | 64 | 9 |
| Comp. Ex. 2 | Impregnation method | 33 wt % $(Mo_{12}Bi_{0.75}Fe_{1.48}Co_{6.52}K_{0.7}O_x)$ | 1.1 g/cc | 1.5 nm | 5 | 60 | 3 |
| Comp. Ex. 3 | Impregnation method | 33 wt % $(Mo_{12}Bi_{0.75}Fe_{1.48}Co_{6.52}K_{0.7}O_x)$ | 0.2 g/cc | 16 nm | 80 | 80 | 64 |
| Comp. Ex. 4 | Sol-gel method | 33 wt % $(Mo_{12}Bi_{1.0}Fe_{3.0}Co_{4.5}Ni_{2.5}K_{0.1}P_{0.5}O_x)$ | 0.49 g/cc | 5.8 nm | 12 | 58 | 7 |
| Comp. Ex. 5 | Impregnation method | 33 wt % $Bi_2O_3 \cdot MoO_3$ | 0.49 g/cc | 5.8 nm | 10 | 50 | 5 |

In above Table 5, the catalysts of Examples 1 to 7 had a remarkably high conversion rate of propylene and remarkably high selectivity and yield of acrylonitrile compared to the catalysts of Comparative Examples 1, 2, 4 and 5.

Considering all with the results of above Table 4, it can be understood that the preparation of a catalyst having a narrow particle size distribution and excellent wear resistance contributes to remarkably increasing the conversion rate of propylene, and selectivity and yield of acrylonitrile.

However, the catalyst of Comparative Example 3 was prepared by using a silica support having a large pore diameter of 16 nm and thus catalytic activity was high. Accordingly, in the reaction carried out on a laboratory scale, it was possible to increase the conversion rate of propylene and the selectivity and the yield of acrylonitrile as shown in above Table 4.

However, as the pore diameter of the silica support is large, the apparent density and durability are lowered, and thus the catalyst may be easily abraded and micronized in the fluidized bed reactor. Accordingly, it is necessary to continuously replenish the catalyst in the mass production of acrylonitrile, and even if the catalyst is added, there is a limit to increasing the yield of acrylonitrile.

Thus, in the mass production of acrylonitrile, catalytic stability may be increased and the conversion rate of propylene and the selectivity and yield of acrylonitrile may be adjusted to a desired range by controlling the pore diameter, apparent density, etc. of the silica support within the range of one embodiment described above with reference to Examples.

The invention claimed is:

1. An ammoxidation catalyst for propylene comprising:
a silica support containing a pore having a diameter of 2 to 15 nm and an apparent density of 0.25 to 1.0 g/cc; and a metal oxide represented by the following Chemical Formula 1 supported on the silica support, $$Mo_{12}Bi_aFe_bA_cB_dC_eO_x; \qquad \text{Chemical Formula 1:}$$

wherein in Chemical Formula 1,
A is at least one element of Ni, Mn, Co, Zn, Mg, Ca and Ba,
B is at least one element of Li, Na, K, Rb and Cs,
C is at least one element of Cr, W, B, Al, Ca and V,
a to e and x are each a fraction of an atom or atomic group, a is 0.1 to 5, b is 0.1 to 5, c is 0.01 to 10, d is 0.01 to 2, e is 0 to 10, and x is 24 to 48.

2. The ammoxidation catalyst of claim 1, wherein the silica support contains a pore having a diameter of 2 to 13 nm.

3. The ammoxidation catalyst of claim 1, wherein the silica support has an apparent density of 0.3 to 1.0 g/cc.

4. The ammoxidation catalyst of claim 1, wherein the silica support has a D50 particle diameter of 50 to 150 μm.

5. The ammoxidation catalyst of claim 1, wherein the silica support has an ammonia ($NH_3$) desorption amount of 1.3 mmol/g or less, and greater than 0.0, measured by an ammonia temperature programmed desorption method.

6. The ammoxidation catalyst of claim 1, wherein the Chemical Formula 1 is the following Chemical Formula 1-1:

$$Mo_{12}Bi_aFe_bCo_cK_dO_x \qquad \text{Chemical Formula 1-1}$$

in the Chemical Formula 1-1, each definition of a to d and x is the same as in claim 1.

7. The ammoxidation catalyst of claim 1, wherein a weight ratio of the metal oxide to the silica support is 15:85 to 35:65.

8. The ammoxidation catalyst of claim 1, wherein the catalyst comprises:

a silica support containing a second pore;

an inner coating layer continuously coating a wall surface of the second pore and comprising the metal oxide represented by the Chemical Formula 1; and a first pore positioned inside the second pore and occupying an empty space excluding the inner coating layer.

9. The ammoxidation catalyst of claim 1, wherein the catalyst has a D10 particle size, a D50 particle size and a D90 particle size satisfying a relationship of Equation 1 below:

$$(D90-D10)/D50 \leq 2.0 \qquad \text{Equation 1.}$$

10. The ammoxidation catalyst of claim 1, wherein the catalyst has an attrition loss of 10% or less according to an ASTM9797-00 method.

11. A manufacturing method of an ammoxidation catalyst for propylene comprising the steps of:

preparing a first precursor aqueous solution containing a Mo precursor;

preparing a second precursor aqueous solution containing a Bi precursor, a Fe precursor, an A precursor, and a B precursor, wherein the A precursor comprises at least one of Ni, Mn, Co, Zn, Mg, Ca, and Ba, and the B precursor comprises at least one of Li, Na, K, Rb and Cs;

supporting a mixture of the first and second precursor aqueous solutions on a silica support containing a pore having a diameter of 2 to 15 nm and an apparent density of 0.25 to 1.0 g/cc;

drying the silica support on which the mixture of the first and second precursor aqueous solutions is supported; and calcining the dried material.

12. The manufacturing method of claim 11, wherein in the preparing of the second precursor aqueous solution, the second precursor aqueous solution contains a Bi precursor, a Fe precursor, a Co precursor, and a K precursor.

13. The manufacturing method of claim 11, wherein in the preparing of the second precursor aqueous solution, the second precursor aqueous solution further contains a C precursor, wherein the C precursor comprises at least one of Cr, W, B, Al, Ca and V.

14. The manufacturing method of claim 11, wherein the mixture of the first and second precursor aqueous solutions has a molar ratio of the metals satisfying a stoichiometric molar ratio of the following Chemical Formula 1:

$$Mo_{12}Bi_aFe_bA_cB_dC_eO_x \qquad \text{Chemical Formula 1}$$

in the Chemical Formula 1,

A is at least one element of Ni, Mn, Co, Zn, Mg, Ca and Ba,

B is at least one element of Li, Na, K, Rb and Cs,

C is at least one element of Cr, W, B, Al, Ca and V, a to e and x are each a fraction of an atom or atomic group, a is 0.1 to 5, b is 0.1 to 5, c is 0.01 to 10, d is 0.01 to 2, e is 0 to 10, and x is 24 to 48.

15. The manufacturing method of claim 11, wherein the drying of the silica support on which the mixture of the first and second precursor aqueous solutions is supported comprises the steps of:

primarily vacuum-drying the silica support on which the mixture of the first and second precursor aqueous solutions is supported at 120 to 160 mbar; and secondarily vacuum-drying the primarily vacuum-dried material at 30 to 50 mbar.

16. The manufacturing method of claim 15, further comprising a step of tertiarily drying the secondarily vacuum-dried material at atmospheric pressure.

17. The manufacturing method of claim 11, wherein the calcining of the dried material is carried out at 500 to 700° C.

18. An ammoxidation method of propylene, comprising the step of reacting propylene and ammonia in the presence of the catalyst of claim 1 in a reactor.

\*  \*  \*  \*  \*